(12) United States Patent
Shalaby et al.

(10) Patent No.: US 6,551,610 B2
(45) Date of Patent: *Apr. 22, 2003

(54) MULTIFACETED COMPOSITIONS FOR POST-SURGICAL ADHESION PREVENTION

(75) Inventors: Shalaby W. Shalaby, Anderson, SC (US); Waleed S. W. Shalaby, Philadelphia, PA (US); Marc Shalaby, Schnecksville, PA (US)

(73) Assignee: Poly-Med, Inc., Anderson, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/131,657

(22) Filed: Apr. 24, 2002

(65) Prior Publication Data

US 2002/0164365 A1 Nov. 7, 2002

Related U.S. Application Data

(60) Continuation-in-part of application No. 09/016,439, filed on Jan. 29, 1998, now Pat. No. 6,413,539, which is a continuation-in-part of application No. 08/740,646, filed on Oct. 31, 1996, now Pat. No. 5,714,159, which is a division of application No. 08/421,222, filed on Apr. 13, 1995, now Pat. No. 5,612,052.

(51) Int. Cl.$^7$ ................................. A61F 2/00
(52) U.S. Cl. ............... 424/426; 424/78.06; 424/78.07; 424/78.17; 514/2; 514/9; 514/12; 514/13; 514/14; 514/15; 514/16; 528/354; 528/361; 525/439; 525/450
(58) Field of Search ............... 424/426, 78.06, 424/78.07, 78.17; 514/2, 9, 12–16; 528/354, 361; 525/439, 450

(56) References Cited

U.S. PATENT DOCUMENTS

| | | | |
|---|---|---|---|
| 3,991,766 A | 11/1976 | Schmitt et al. | 128/335.5 |
| 4,141,973 A | 2/1979 | Balazs | 424/180 |
| 4,209,607 A | 6/1980 | Shalaby et al. | 528/291 |
| 4,226,243 A | 10/1980 | Shalaby et al. | 128/335.5 |
| 4,369,229 A | 1/1983 | Shah | 428/421 |
| 4,532,134 A | 7/1985 | Malette et al. | 514/55 |
| 4,911,926 A | 3/1990 | Henry et al. | 424/426 |
| 4,919,939 A | 4/1990 | Baker | 424/493 |
| 4,937,254 A | 6/1990 | Sheffield et al. | 514/420 |
| 4,938,763 A | 7/1990 | Dunn et al. | 604/891.1 |
| 4,994,277 A | 2/1991 | Higham et al. | 424/443 |
| 5,011,692 A | 4/1991 | Fujioka et al. | 424/426 |
| 5,077,049 A | 12/1991 | Dunn et al. | 424/426 |
| 5,093,319 A | 3/1992 | Higham et al. | 514/55 |
| 5,135,752 A | 8/1992 | Snipes | 424/435 |
| 5,171,148 A | 12/1992 | Wasserman et al. | 433/215 |
| 5,198,220 A | 3/1993 | Damani | 424/426 |
| 5,278,201 A | 1/1994 | Dunn et al. | 523/113 |
| 5,366,733 A | 11/1994 | Brizzolara et al. | 424/426 |
| 5,366,756 A | 11/1994 | Chesterfield et al. | 427/2.26 |
| 5,385,738 A | 1/1995 | Yamahira et al. | 424/489 |
| 5,612,052 A * | 3/1997 | Shalaby | 424/425 |
| 5,714,159 A * | 2/1998 | Shalaby | 424/425 |
| 5,866,544 A | 2/1999 | Goodbody et al. | 514/16 |
| 6,037,331 A | 3/2000 | Shalaby et al. | 514/54 |
| 6,413,539 B1 * | 7/2002 | Shalaby | 424/426 |

* cited by examiner

*Primary Examiner*—Samuel A. Acquah
(74) *Attorney, Agent, or Firm*—Leigh P. Gregory

(57) ABSTRACT

This invention deals with an absorbable, gel-forming composition for multifaceted prevention of post-operative surgical adhesion through a plurality of physico-pharmacological modes, comprising a solution of one or more bioactive compounds in a liquid copolymeric vehicle made by end-grafting one or more cyclic monomer onto a polyalkylene glycol. More specifically, the bioactive drugs can display one or more pharmacological activity associated with antiangiogenic, antineoplastic, anti-inflammatory, and anti-proliferative effects.

22 Claims, No Drawings

MULTIFACETED COMPOSITIONS FOR POST-SURGICAL ADHESION PREVENTION

FIELD OF INVENTION

This application is a continuation-in-part of U.S. patent application Ser. No. 09/016,439 entitled Hydrogel-forming, Self-Solvating Absorbable Polyester Copolymers and Methods for Use Thereof, filed on Jan. 29, 1998 now U.S. Pat. No. 6,413,539, which is a CIP of U.S. patent application Ser. No. 08/740,646, filed on Oct. 31, 1996, now U.S. Pat. No. 5,714,159, which is a division of application Ser. No. 08/421,422, filed on Apr. 13, 1995, now U.S. Pat. No. 5,612,052.

This invention relates to biomedical and/or pharmaceutical applications of absorbable or biodegradable polymeric hydrogels. More particularly, the present invention relates to hydrogel-forming, self-solvating absorbable polyester copolymers capable of selective segmental association into compliant hydrogel upon contacting an aqueous environment. The invention also discloses using the polyester copolymers in combination with other agents to provide novel, multifaceted compositions capable of preventing post-surgical adhesion (or post-operative adhesion, POA) in humans through the simultaneous display of four or more of the key properties associated with individual anti-adhesion systems known in the prior art.

BACKGROUND OF THE INVENTION

In 1988, a national hospital discharge survey estimated that postoperative adhesions contributed to 282,000 hospital admissions for adhesiolytic abdominal surgery, nearly one million days of in-patient care, and 1.2 billion dollars in expenditures. It is expected that these figures have increased despite surgical and adjuvant strategies to decrease the incidence of adhesions. A recent retrospective study examined hospital re-admissions from a group of 29,790 patients who underwent abdominal or pelvic surgery in 1986. From this group, 34% were readmitted over a ten year period for disorders directly or possibly related adhesion complications. Although 58% of this cohort required only one readmission, 44% had 2 to 5 admissions. The most severe complication was a small bowel obstruction in which 64% of the patients required additional surgery. In addition, the sites of initial surgery were equally distributed among mid/hindgut, foregut, and female reproductive tract. It has been estimated that up to 54% of all intestinal obstructions are secondary to adhesions bands from prior surgery. To date, no prospective study has shown a decrease in the incidence of intestinal obstruction using adjuvants designed to reduce postoperative adhesions.

The clinical statistics noted above and other data show clearly that postoperative adhesions (POA) are significant complications in most surgical procedures. Among the most common and widely addressed types of POA are the peritoneal types, which are the leading cause of intestinal blockage or obstruction. Equally important types of POA are encountered following gynecological surgery, which can lead to infertility, chronic pain, and obstructive disorder. Pericardial POA received relatively less attention than the two aforementioned types. On the other hand, minor, but growing, interest has been directed to adhesions such as those experienced in the thorax and tendons and vertebra. Although POA can be minimized by following careful surgical techniques, several non-surgical approaches have been used with variable levels of success. Some of the non-surgical approaches to prevent POA focused on the prevention of fibrin deposition as a strategy to prevent post-surgical adhesion. These strategies included the use of anticoagulants and irrigation, and the separation of tissue surfaces using (1) Dextran® lavage in intraperitoneal procedures; (2) oxidized cellulose films, e.g., Interceed; (3) carboxymethyl cellulose solution; (4) chondroitin sulfate solutions; (5) polyvinyl pyrrolidone solutions; (6) Polyoxamer 407 solutions; and (7) Gortex films. Other approaches to prevent post-surgical adhesions have relied on the (1) removal of fibrin matrix through the use of fibrinolytics and proteolytic enzymes or tissue-type plasminogen activator.

Developing appropriate and effective therapies for inhibiting inflammation and adhesion formation is still a major challenge. While NSAIDs (non-steroidal anti-inflammatory drugs) have been shown to decrease the tissue inflammatory response and enhance fibrinolytic potential in peritoneal tissues, previous studies have shown that these drugs need to be delivered to specifically targeted areas for several days to be effective. In turn, while hyaluronic acid has demonstrated potential as a drug carrier, the concentrations and molecular weights required for biological efficacy prohibit the practical use of this compound in an injectable form. A moderately effective strategy for preventing POA in rats entailed the local administration of non-steroidal anti-inflammatory drugs, such as Tolmetin®, as part of a controlled release system (U.S. Pat. No. 4,937,254). A promising strategy for preventing POA in flexor tendons was explored by Shalaby and coworkers (U.S. Pat. Nos. 6,037,331 and 5,866,544) entailed use of a locally administered controlled release system of bioactive agents (including NSAID) in moderate viscosity gel-forming hyaluronic acid systems as a transient barrier matrix. The promising results associated with the latter strategy and availability of a novel class of liquid, absorbable gel-forming copolyesters, which have been successfully used by Shalaby and coworkers on a transient matrix for the controlled release of bioactive agents (U.S. Pat. Nos. 5,612,052 and 5,714,159) contributed to the conceptual development of the present invention.

Growing interest in developing absorbable pharmaceutical surgical products which degrade in the biologic environment to safe by-products without residual mass remaining at the application site justified the search for novel, absorbable gels. In a recent disclosure, a novel gel-former was described to be based on absorbable copolymers which, upon hydration, result in hydrogels that are stabilized by pseudo-crosslinks provided by a hydrophobic polyester component covalently linked to a hydrophilic component made of pharmaceutically acceptable polymer, such as polyoxyethylene. The polyester component is made of safe monomers, such as p-dioxanone, ε-caprolactone, glycolide, lactide, trimethylene carbonate, and mixtures thereof. Contrary to a related study, which describes in situ formation of biodegradable, microporous, solid implants in a living body through coagulation of a solution of a polymer in an organic solvent such as N-methyl-2-pyrrolidine, the new hydrogel-former does not require the use of solvents. Such solvents did include low molecular organic compounds that can migrate from the application site and cause cell dehydration and tissue necrosis. Equally important is the fact that previously known systems are solid implants which can elicit mechanical incompatibility and, hence, patient discomfort as compared with the new compliant, swollen, mechanically compatible hydrogels.

The use of absorbable gel-formers may very well lead to some of the most important applications of absorbable polymers in the pharmaceutical and biomedical industries. Among the inventor disclosed current activities in this area are uses of the gel-formers in (1) periodontal application of antibiotics; (2) antibiotics formulations for osteomyelitis, (3) intraocular drug delivery; (4) wound healing and hemostasis; (5) controlling the release of insulin; and (6) controlling the bioavailability of ricin A-chain.

Adhesion formation after abdominal surgery is a significant cause of post-operative morbidity. In gynecological surgery, adhesion can lead to infertility, chronic pain, and obstructive disorder. Numerous adhesion prevention adjuvants have been investigated, most of which are based on pharmacological agents or protective barriers. However, the combined effect of a transient barrier and pharmacological agent using a local controlled release system was practically unexplored. Meanwhile, analysis of the different theories on the cause and prevention of post-surgical adhesion and critical review of numerous attempts to achieve different levels of efficacy by many investigators led the present inventor to conceptualize that an ideal system for post-surgical adhesion prevention must meet a least four of the following requirements: (1) ease of application as a liquid that transforms into a three-dimensional compliant gel upon administration to a surgical site; (2) formation of a temporary barrier which exhibits barrier properties for up to 72 hours; (3) exhibiting mild adhesive properties toward traumatized tissue; (4) dissolves or disperses into a mechanically biocompatible components; (5) yielding minimum acidic by-products; (6) dissolving the bioactive agent; (7) allowing the release of a bioactive agent in two modes, an initial burst followed by additional release for up to 72 hours; and (8) the bioactive agent is (a) a non-steroidal, anti-inflammatory drug (NSAID), and/or (b) an anti-angiogenic agent, that retards or inhibits temporarily cell growth, proliferation, and neovascularization at non-toxic doses. To date, however, only up to three of these requirements have been met by any of the systems known in the prior art; this can be deduced from the following summaries of the disclosed prior art. On the other hand, the multifaceted compositions subject of this invention do meet at least four of these requirements. More specifically, the gel-forming liquid vehicles for the compositions of the present invention, which are also disclosed in U.S. Pat. Nos. 5,612,052 and 5,714,159 and patent application Ser. No. 09/016,439, do meet the requirements dealing with (1) consistency and ease of application; (2) transient barrier properties; (3) releasing minimum acidic by-products; (4) mild-adhesion to tissue; and (5) absorption or dispersion into biomechanically biocompatible components within 48 hours. Additionally, the gel-former/bioactive combination does meet the solubility drug release requirement and the bioactive agent has at least one of the desirable pharmacological effects.

To provide the basic information that led the present inventor to conceive the requirements in an ideal system for preventing post-surgical adhesion, given below are analyses of key biological events relevant to post-surgical adhesion and different approaches to its prevention. These include (1) mechanisms of adhesion formation; (2) adhesion prevention; and (3) advances in the effect of bioactive agents on adhesion prevention.

The process of peritoneal wound healing requires 5 to 8 days after surgical injury. It is generally agreed that the critical step in adhesion formation occurs during this period. The first stage or inflammatory phase is characterized by increased vascular permeability resulting in the production of serosanguinous and proteinaceous exudates. Mediators of this process include histamine and prostaglandins. The coagulation phase follows within three hours of injury leading to the formation of a fibrinous mass infiltrated with inflammatory cells. It is believed that the fibrin acts as a scaffolding moiety for cell migration and recruitment. Over the next 24–48 hours, cell migration and organization occurs. Fibrinolysis occurs by day 3 with concomitant fibroblast proliferation. Repair of the wound defect begins by day 2 or 3 and is characterized by islet formations of mesothelial cells. Healing is multifocal as opposed to healing from the wound edge. The process is complete by 5 to 8 days.

The common denominator for adhesion formation begins with the inefficient transformation from the fibrin clot to its degradation products. Animal and human data have shown that this reflects a decrease in the activity of tissue plasminogen activator (tPA) and an increase in the activity of plasminogen activator inihibitor-1. It has been shown that a 70% reduction in adhesion formation can be achieved when recombinant tPA was added to intraperitoneally administered hyaluronic acid. However, it was later shown that the strength of the healing wound was significantly compromised at doses required to prevent adhesions.

The cellular events in wound healing are mediated by an array of cytokines functioning as chemoattractants and immunostimulants. Their role in adhesion formation has become increasingly apparent in recent years. Adhesiogenic cytokines have included interleukin-6 and interleukin-1a, transforming growth factor-$\alpha$, and transforming growth factor-$\beta$, epidermal growth factor, and tumor necrosis factor-$\alpha$. Interleukin-10 has been shown to reduce adhesion formation by inhibiting the formation of IL-1, IL-6, and TNF-$\alpha$. Various non-steroidal anti-inflammatory agents have also been shown to reduce adhesion formation. Thus, the use of agents that inhibit the inflammatory cascade my have a unique role in minimizing the formation of adhesions.

Surgical efforts to minimize postoperative adhesions have been limited. It was originally felt that separate closure of the peritoneal defect after laparotomy would decrease adhesion formation, and hence, adhesion-related complications such as intestinal obstructions. However, multiple animal and human studies have shown that nonclosure of the peritoneum is not detrimental in terms of adhesion formation or postoperative complications. The argument against closure is that the peritoneum heals rapidly without separate reapproximation, there is less tissue handling and suture placement with nonclosure, as well as decreased operative time. Furthermore, the presence of excess suture can cause tissue strangulation/ischemia which promotes adhesion formation. For this reason, reperitonealization of raw surfaces after dissection is no longer the standard of surgical practice. Studies comparing laparoscopy versus laparotomy (pfannenstiel or vertical incision) have shown dramatic decreases in the formation of anterior abdominal wall adhesions. However, morbidity outcomes have not been studied to date. Second-look procedures to evaluate the efficacy of adhesiolysis have indicated reformation rates as high as 97% irrespective of surgical technique (microsurgical versus laser). Although adhesion reformation rates are high, improved fertility has been observed.

The marginal improvements seen with improved surgical technique prompted a wide range of adjuvant strategies. Early studies focused on the intraperitoneal administration of crystalloid or colloid solutions to minimize tissue-tissue contact by creating a thin film. It was expected that the presence of a thin film would minimize contact between raw surfaces, and thus, inhibit adhesion formation. To date, however, numerous studies have shown no proven efficacy. Examples include phosphate buffered saline, lactated ringer's, normal or hyperosmotic saline, and dextran 70.

Furthermore, the addition of heparin had no influence on adhesion formation. In practice, these solutions are rapidly absorbed from the peritoneum, and thus, any potential efficacy from a thin filmy layer is lost. It is estimated that the peritoneal cavity absorbs up to 500 cc of physiologic saline in less than 24 hours. Thus, it is not surprising that crystalloid/colloid solutions are ineffective given that peritoneal wound healing/adhesion formation requires up to 5 to 8 days. Given the apparent importance of inflammation, it was felt that inhibiting their response would decrease adhesion formation. Modulating the inflammatory response was first studied using corticosteroids without success. However, nonsteroidal anti-inflammatory agents (NSAIDs) and other immunomodulators have recently shown decreased adhesion formation in animal models. These include low-dose aspirin, ketorolac and IL-10, monocyte chemotactic protein 1, antibodies to vascular permeability factor, and antioxidants. Agents designed to promote fibrinolysis have also demonstrated efficacy in animal models. These strategies range from the use of t-PA to inhibitors of collagen synthesis and thrombin formation.

The concept of using mechanical barriers to prevent the apposition of raw intra-abdominal surfaces has received considerable interest. While tissue barriers such as omental grafts have not proven useful, much of our current interest has focused on various synthetic barriers. It can be appreciated that the ideal barrier would be expected to eliminate adhesion formation, exhibit ease of handling, application, and retention at the site(s) of interest, applicable to both open surgical or laparoscopic procedures, and biodegradable to facilitate removal. To date, the ideal barrier has yet to be developed. Currently available products have shown only a modest reduction in adhesion prevention. Sites of interest have included the anterior abdominal wall after vertical incisions, the uterus after myomectomy and associated adnexal structures after adhesiolysis. Prospective studies are currently underway to correlate these strategies with morbidity; however, have been marginally quantified in terms of fertility. The list of available synthetic barriers are Seprafilm® (carboxymethylcellulose/hyaluronic acid), Interceed® (oxidized regenerated cellulose), and Gore-tex Surgical Membrane® (expanded polytetrafluoroethylene,), and Intergel® (ionically crosslinked hyaluronic acid). While only a marginal decrease in adhesions are noted, these material suffer from additional shortcomings including ease of handling (Seprafilm), retention at tissue surface (Interceed), compromised efficacy in the presence of blood (Interceed), secondary surgery for removal (Gore-tex Surgical Membrane), and limited application to conservative surgery (Intergel®). A number of materials have shown promise in clinical and animal studies. These include Sepracoat® (hyaluronic acid gel), ferric hyaluronate, crosslinked hyaluronic acid (Incert®), and photopolymerized hydrogels.

In a recent study on the effect of octreotide, a long-acting analogue of somatostatin, on postoperative adhesion formation was investigated. The rationale was based on its known modulatory effects on collagen synthesis. Components of this study can be summarized as follows: SUBJECTS: Male Swiss albino mice. INTERVENTIONS: Both sides of a 5-cm ileal segment from Swiss albino mice were scraped 10 times, and transient ischemia was induced by clamping the segmental artery. Animals were injected subcutaneously with 1 mL/d of saline for 3 days (group 1), a single 5-mL intraperitoneal dose of saline (group 2), subcutaneously with 10 micrograms/kg daily of octreotide for 3 days (group 3) or a single 10 micrograms/kg intraperitoneal dose of octreotide (group 4). In half of the animals repeat laparotomy was performed on postoperative day 5 After adhesions were graded, the scraped ileal segments were excised for determination of hydroxyproline quantity. The same procedure was repeated on postoperative day 14 for the remaining animals. OUTCOME MEASURES: Adhesion grading, hydroxyproline levels. RESULTS: On postoperative day 5, the intraperitoneal octreotide group (group 4) had a significantly lower median adhesion score than groups 1 and 2. On postoperative day 14, both octreotide groups (3 and 4) had a significantly lower median adhesion grading than both saline groups (1 and 2). Hydroxyproline levels of the groups were not significantly different on either day 5 or day 14. CONCLUSION: Octreotide has a beneficial effect in decreasing adhesion formation in the early postoperative period.

Another study examined the influence of octreotide on adhesion prevention through inhibition of glycosaminoglycan synthesis by fibroblasts. Basic elements of this study can be summarized as follows: METHODS: Twenty-four male Wistar rats were divided into four groups. Laparotomy with a 15-cm intestinal resection and reanastomosis was performed on each group of rats. The intestinal serosa was also scratched to induce adhesion formation. No medication was given to group-1 rats (C). Group-2 rats received peritoneal irrigation with 6 ml normal saline intraoperatively (NS). Group-3 rats received irrigation with 6 ml octreotide solution (5 micrograms/ml) intraperitoneally (Oc). Group-4 rats received irrigation with 6 ml octreotide solution intraoperatively and 10 micrograms/kg of octreotide injection intramuscularly twice a day for 14 days (Oc+IM). All rats were euthanized 2 weeks later. The number of fibrous bands at and away from the anastomotic site was recorded. The strength and extent of the fibrous bands were also measured. RESULTS: The total scores of intraperitoneal adhesion bands were significantly reduced in group Oc and group Oc+IM rats when compared with group C ($p<0.05$). When the fibrous bands at the anastomotic site and away from it were distinguished, the results were the same. As to the strength and extent of intestinal adhesions, the data showed no significant difference among all four groups. CONCLUSIONS: These data supported the suggestion that octreotide can reduce the incidence of postoperative intraperitoneal adhesions in rats.

Inhibition of fibrinolysis is known to be a major mechanism for postoperative adhesion formation. Because aprotinin inhibits fibrinolysis, it may lead to an increase in adhesion formation whereas its anti-inflammatory effects may lead to a decrease in adhesion formation. A recent study attempted to clarify conflicting results in previous literature. Segments of this study can be summarized as follows: METHODS: Basal levels of intestinal hydroxyproline (OHP) content and local fibrinolytic activity (LFA) were determined using naive groups. In the experimental groups, adhesions were created by scraping and creating a transient ischemia of a segment of terminal ileum. Group I and II rats were injected subcutaneous (s.c.) normal saline (NS) for 3 days and single dose intraperitoneal (i.p.) NS, respectively. Group III and IV rats were injected s.c. aprotinin for 3 days and single dose i.p. aprotinin, respectively. Group V rats were injected intramuscular methylprednisolone (MP) for 3 days. LFA and OHP levels were determined on the second and fifth postoperative days. The severity of adhesion formation was graded on the fifth day. RESULTS: Aprotinin decreased both the severity of adhesions and OHP levels whereas MP decreased only the severity of adhesions. There was an early depression of LFA at the second day in both NS and MP groups increasing to basal levels at the fifth day.

OHP levels showed significant correlation with adhesion severity. CONCLUSION: Results showed that aprotinin decreased intra-abdominal adhesion formation probably by preventing early depression of LFA.

In a study of macromolecular conjugates of cis-4-hydroxy-L-proline (cHyp) as antifibrotic agents, the results suggest the controlled release of covalently linked cHyp from the polymeric chain increases its bioavailability and, hence, antifibrotic activity. This, in turn, suggests the potential use of this system to prevent POA adhesions.

SUMMARY OF THE INVENTION

The primary objective of the present invention is to provide a composition comprising one or more bioactive agents in a hydrogel-forming self-solvating absorbable copolymer capable of segmental association into a compliant, thin hydrogel membrane when in contact with the aqueous environment of a traumatized surgical site to prevent post-surgical adhesion formation.

A specific aspect of this invention deals with a hydrogel-forming, self-solvating, absorbable composition for preventing/minimizing post-surgical adhesion comprising an oligopeptide made of 6 to 32 amino acids. A more specific aspect of this invention deals with a composition for preventing/minimizing post-surgical adhesion comprising an oligopeptide that is a somatostatin analog. A specific aspect of this invention deals with an absorbable, gel-forming composition comprising one or more of the cyclic octapeptide cited by R. Barrie et al [*J Surgical Res.*, 55, 446 (1993)] as effective antiangiogenic peptide and particularly those denoted as RC-160, SMS 201–995, BIM 23014, and RC-121. A more specific aspect of this invention deals with an absorbable gel-forming composition comprising one or more cyclic octapeptide having the following amino acid sequences and preferably comprising (1) a cystine bridge between positions 2 and 7; and (2) a lysine residue in position 5:

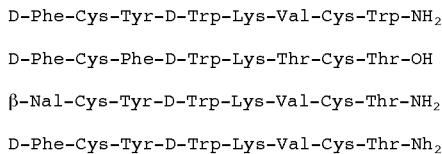

Where Nal=3-(2-naphthyl)-ALa.

Another more specific aspect of this invention deals with a composition for preventing/minimizing post-surgical adhesion comprising the somatostatin analog known in commerce as Lanreotide, at concentrations of less than 0.5 mg/mL and preferably at about 0.25 mg/mL. Another specific aspect of this invention deals with a hydrogel-forming composition for preventing/minimizing post-surgical adhesion comprising a non-steroidal anti-inflammatory drug, such as naproxen, at a concentration of less than 5 mg/mL or preferably between 2 and 3 mg/mL. A more specific aspect of this invention deals with a composition for preventing/minimizing post-surgical adhesion comprising an anti-proliferation drug, such as paclitaxel, at a concentration of less than 50 mg/mL and preferably about 30 mg/mL. Another aspect of this invention deals with a hydrogel-forming composition containing a bioactive agent with more than one pharmacological effect such as trapidil. Another aspect of this invention deals with a salt of a basic somatostatin analog wherein the acid component is an anti-inflammatory drug such as naproxen.

A preferred composition of a multifaceted system for preventing POA comprises (1) a gel-forming carrier made by the end-grafting of liquid polyethylene glycol (PEG) with a mixture of trimethylene carbonate (TMC) and glycolide (G); and (2) an oligopeptide consisting of 6–32 amino acid units. A more preferred composition comprises a mixture of a PEG/TMC/G copolyester with a PEG content of more than 50% and a second copolyester where the PEG is less than 50% of the mass of the polymeric chain. A preferred mixture of these copolyesters is one that (1) adheres slightly to the surgical site as a thin, transient barrier for up to 72 hours. A most preferred composition comprises the mixed gel-forming vehicle and a somatostatin analog as a fatty acid salt such as an acetate, propionate, or octanoate and more specifically lanreotide and other cyclic octapeptides cited by R. Barrie et al. [*J. Surg. Res.*, 55, 446 (1993)] as the somatostatin analogs capable of inhibiting angiogenesis. Another preferred composition comprises a mixed gel-forming vehicle and lutenizing human releasing hormone (LHRH) analog as a salt of a fatty acid. Other similar versions of gel-formers are those made from PEG (or block copolymers with polypropylene glycol) and one or more of the following cyclic monomers: lactide, F-caprolactone, p-dioxanone, 1,5-dioxepan-2-one, trimethylene carbonate, and glycolide.

Another preferred composition of a multifaceted system comprises a (1) gel-forming PEG copolyester, such as those noted above, which upon hydrolytically driven absorption releases a minimum amount of glycolic acid (or lactic acid); and (2) an NSAID. A more preferred composition comprises the mixed gel-forming PEG/G/TMC copolyester and carboxyl-bearing NSAID and most preferably, the NSAID is naproxen.

Another preferred composition comprises a gel-forming vehicle, such as one of those noted above, and an antiangiogenic peptide that exists as the salt of a carboxyl-bearing NSAID. A more preferred composition is one that comprises a somatostatin analog (SA) as a salt of the free acid form of an NSAID such as naproxen.

Another preferred composition comprises (1) the mixed gel-forming vehicle described above after being end-acylated with dicarboxylic anhydride, such as glutaric and/or succinic anhydride, to create covalently bound carboxylic end-groups capable of forming an ionic conjugate with a basic antiangiogenic peptide, such as a somatostatin analog and more specifically lanreotide. A more preferred composition is one where the gel-forming copolymer is partially acylated with cyclic anhydride and comprising two types of ionic conjugates of a basic peptide, such as lanreotide or other somatostatin analogs: one with gel-forming carboxylate end-groups and a second with a carboxylic-bearing NSAID, such as the free acid form of naproxen.

Another preferred gel-forming composition comprises any of the gel-forming copolyesters described above in which the chain is free-radically grafted with maleic anhydride) maleation) to yield a succinic acid-bearing chain after undergoing mild hydrolysis. The maleation of the gel-former can be controlled to provide sufficient sites for ionic conjugation with one or more basic peptide such as lanreotide and other somatostatin analogs.

Another preferred composition comprises any of the gel-forming vehicles described above and anti-proliferative drugs. A more preferred composition is one where the anti-proliferative drug is paclitaxel. A most preferred composition comprises any of the gel-forming vehicles described above and a pharmacologically active compound that displays an anti-inflammatory function as well as being capable of retarding cell aggregation as for example, trapidil.

Another preferred composition comprises any of the above noted gel-forming liquids and an interleukin such as interleukin-4 (IL-4). A more preferred composition is one that contains IL-4 with an NSAID such as naproxen.

DETAILED DESCRIPTION OF THE INVENTION

The term "multifaceted composition" as used herein refers to a composition that (1) displays one or more pharmacological activity; (2) supports a physical or mechanical function, such as being a physical barrier , and (3) provides a unique control of integrated pharmacological, biological, and physical events. The term "gel-forming liquid copolyester" as used herein refers to materials which absorb solvents, such as water, undergo phase transformation, and maintain three-dimensional networks capable of reversible deformation. Depending on the type of employed gel-forming system, whether it is a single or multiple copolymeric component, those preferred for preventing POA can be tailored to provide a thin, lightly attached barrier membrane. The latter is expected to maintain its properties for up to 72 hours. The pharmacological activity of the systems subject of this invention are expected to be attained by incorporating one or more biologically active compound which preferably dissolves in the gel-forming vehicle or is capable of forming a soluble ionic conjugate with at least a fraction of the functional groups of the carboxyl-bearing gel-forming vehicle. Among the useful bioactive agents are peptides, including LHRH (e.g., tryptoroline), somatostatin analogs (e.g., lanreotide and octreotide), and bombesin. An important aspect of this invention is the incorporation of cyclic octapeptide in the gel-forming vehicle wherein these peptides directly inhibit angiogenesis and indirectly mediate inflammation and exhibit anti-neoplastic function at the surgical site. Another group of bioactive agents includes (1) potent, non-steroidal anti-inflammatory drugs (e.g., naproxen, Tolmetin); (2) anti-neoplastic/anti-proliferative drugs (e.g., paclitaxel); (3) drugs which exhibit more than one mode of pharmacological activity, such as trapidil, which is an anti-inflammatory drug that inhibits cell aggregation; and (4) interleukin-4 ( IL-4). A preferred form of the bioactive agent is one that is an ionic conjugate of two different bioactive molecules with different mechanisms of action, but can synergistically prevent POA. Typical examples of these ionic conjugates are those comprising (1) a basic peptide (e.g., lanreotide) and an acidic NSAID, such as naproxen; and (2) low molecular weight heparin and a basic peptide.

The preparation of gel-formers is disclosed in U.S. Pat. Nos. 5,612,052, 5,714,159, and U.S. patent application Ser. No. 09/016,439 filed Jan. 29, 1998, the contents of which are incorporated herein by reference. Specific examples of gel-formers are described below. Representative examples of active formulations based on the typical gel-forming compositions and their placebos are described below. The performance of representative formulations in preventing POA using the side-wall rat model are also illustrated in one of the following examples.

The following examples are provided to further illustrate the present invention and should not be construed as limitations thereof.

EXAMPLE 1

Preparation of a Mixed Gel-forming Vehicle Comprising PEG -400 End-grafted with a Mixture of TMC and Glycolide The first step entailed the preparation of relatively hydrophobic copolyester P1 (11.2/88.8 PEG/copolyester). Thus, PEG-400 (45 g) was mixed under a dry nitrogen environment in a predried glass reactor (equipped for mechanical stirring) with TMC (93.2 g, 0.913 mole) and glycolide (11.8 g, 0.102 mole) and stannous octanoate (0.203 mmole as a 0.2 molar solution in dry toluene) as a catalyst. The end-grafting of PEG with the cyclic monomers was conducted at 150° C. for five hours while mixing after the melting of the reaction charge at about 110° C. Using gel permeation chromatography, the conversion of the monomer was shown to be practically complete. Trace amounts of residual monomers were removed by distillation at 110° C. under reduced pressure. The purified polymer was characterized for molecular weight (by GPC), identify (by IR) and composition (by NMR) and exhibited the expected properties based on the polymerization charge.

The second step entailed the preparation of a more hydrophilic copolymer, P2 (80/20 PEG/copolyester) following the same reaction scheme as that described above for P1. However, the polymerization charge consisted of PEG (120 g), TMC (26.6 g, 0.888 mole), glycolide (3.34 g, 0.029 mole) and stannous octanoate (0.203 mmole as 0.2 molar solution in dry toluene).

The third step—selection of P1/P2 mixture. Several compositions comprising different ratios of P1/P2 were made and characterized for (1) bulk viscosity (using capillary rheometry); (2) adhesion to moist substrate (using the fabric peel test cited in Flagle et al [*Trans. Soc. Biomater.,* 22, 376 (1999)]; (3)ability to form a thin hydrogel membrane upon contacting water; (4) retention of the mechanical integrity over 4–48 hours (using an incubator shaker at pH 7.4 and 37° C.); and (5) capacity to dissolve of the different bioactive agents.

EXAMPLE 2

General Method of Preparation of the Bioactive and Placebo Formulation.

A selected mixed gel-forming composition, namely, one that is made of 70/30 P1/P2 was heat sterilized at 120° C. for one hour. The sterile liquid vehicle was allowed to reach room temperature in a laminar flow hood. The specific amount of the bioactive agent was mixed in a closed, sterile container. Complete dissolution of the bioactive agent was achieved by mixing in a sterile container. Typical composition of these formulations are shown in Table I.

EXAMPLE 3

Evaluation of POA Prevention

The different formulations were evaluated for their efficacy in preventing POA in a rat side-wall model. The relevant procedure can be outlined as follows:

Under appropriate anesthesia, a small abdominal incision was made in female Sprague-Dawley to enter the abdominal cavity. A 1 cm$^2$ area of peritoneal side-wall was excised with a scalpel blade. Then a size 6-0 silk suture was stretched around the perimeter of the excised area with a square knot at each corner. The remaining animal protocol and adhesion rating criteria was based on the work of by Burns et al. [*Fertil Steril.,* 66, 814 (1996)].

At one-week post-operatively, the adhesion prevention score was recorded for the different formulations on a scale of 0–10, where approximately 10 represents maximum adhesion using a cyanoacrylate tissue adhesive as a positive control and 0 is used to reflect the absence of any adhesion. The basic feature of the scoring system can be summarized as follows:

Adhesion Scoring—Adhesions to the abdominal sidewall were scored as described by Burns et al. [*Fertil Steril.*, 69, 415–418 (1998)].

Adhesion Score: (AS)
 0=no adhesions or involvement
 1=1%–25% involvement
 2=26%–50% involvement
 3=51%–75% involvement
 4=76%–100% involvement Morphology Score: (MS)
 0=no adhesions
 1=filmy avascular adhesions
 2=vascular or opaque adhesions
 3=cohesive attachment of abraded site with each itself or other structures (intestine and/or sidewall)

Severity Score: (SS)
 0=no adhesions
 1=adhesions separated with gentle traction
 2=adhesions requiring moderate traction to separate
 3=adhesions requiring sharp dissection to separate A total score of 10 is possible based on degree of adhesion involvement, morphology, and severity. The mean total score and each mean categorical score (+/−SEM) was calculated and compared. Statistical significance was determined by the Mann-Whitney U test using a probability value of less than 0.05. To maximize confidence in the in vivo procedure all scoring was completed by the attending veterinarian.

The average scores of representative formulations are summarized in Table I.

TABLE I

Total Adhesion Prevention Scores of Representative Sets of Bioactive and Placebo Formulations[a]

| Composition | Total Score |
| --- | --- |
| Cyanoacrylate Positive Control | 9.6 |
| Silk Suture Control[b] | 7.2 |
| Silk Suture/Vehicle Control, P1/P2 gel-former | 5.1 |
| 30 mg/mL Paclitaxol in 70/30 P1/P2 gel-former | 4.2 |
| 3 mg/mL Trapidil in 70/30 P1/P2 gel-former | 4.0 |
| 3 mg/mL Naproxen in 70/30 P1/P2 gel-former | 2.8 |
| 0.1 mg/mL Tryptoroline in 70/30 P1/P2 gel-former | 2.8 |
| 0.25 mg/mL Lanreotide in 70/30 P1/P2 gel-former | 0.8 |

[a]All formulations were applied as 0.1 mL on to a 1 cm$^2$ area of surgical site.
[b]No formulation was used.

What is claimed is:

1. An absorbable, liquid, gel-forming composition for multifaceted prevention of post-operative surgical adhesion through a plurality of physicopharmacological modes comprising a solution of one or more bioactive compound in a copolymerization product of polyalkylene glycol end-grafted with one or more cyclic monomer.

2. An absorbable, liquid, gel-forming composition as in claim 1 wherein end-grafted polyalkylene glycol is a polyethylene glycol.

3. An absorbable, liquid, gel-forming composition as in claim 2 wherein the polyethylene glycol is end-grafted with a mixture of trimethylene carbonate and glycolide.

4. An absorbable, liquid, gel-forming composition as in claim 3 wherein end-grafted polyethylene glycol is a mixture of two or more types having significantly different polyether/copolyester ratios.

5. An absorbable, liquid, gel-forming composition as in claim 1 wherein the bioactive agent is polypeptide comprising 6 to 32 amino acid sequences.

6. An absorbable, liquid, gel-forming composition as in claim 5 wherein the polypeptide is a somatostatin analog.

7. An absorbable, liquid, gel-forming composition as in claim 6 wherein the somatostatin analog is a cyclic octapeptide at a concentration up to 0.5 mg/mL.

8. An absorbable, liquid, gel-forming composition as in claim 7 wherein the cyclic octapeptide comprises lanreotide.

9. An absorbable, liquid, gel-forming composition as in claim 5 wherein the polypeptide is a lutenizing human releasing hormone (LHRH) analog.

10. An absorbable, liquid, gel-forming composition as in claim 9 wherein the LHRH analog concentration in the vehicle is less than 0.5 mg/mL.

11. An absorbable, liquid, gel-forming composition as in claim 4 wherein the intrachain or terminal sequences are chemically modified to produce carboxyl-bearing molecules.

12. An absorbable, liquid, gel-forming composition as in claim 11 wherein at least a fraction of the carboxylic group forms ionic conjugates with a bioactive peptide.

13. An absorbable, liquid, gel-forming composition as in claim 1 wherein the bioactive agent is a basic polypeptide that is ionically conjugated with a carboxyl-bearing bioactive agent.

14. An absorbable, liquid, gel-forming composition as in claim 13 wherein the polypeptide comprises 6 to 32 amino acid sequences and the carboxyl-bearing bioactive agent is an NSAID.

15. An absorbable, liquid, gel-forming composition as in claim 1 wherein the bioactive agent comprises an NSAID.

16. An absorbable, liquid, gel-forming composition as in claim 1 wherein the bioactive agent comprises an antineoplastic compound.

17. An absorbable, liquid, gel-forming composition as in claim 1 wherein the bioactive agent has more than one pharmacological function.

18. An absorbable, liquid, gel-forming composition as in claim 14 wherein the NSAID comprises naproxen.

19. An absorbable, liquid, gel-forming composition as in claim 8 wherein the lanreotide concentration in the gel-forming vehicle is about 0.25 mg/mL.

20. An absorbable, liquid, gel-forming composition as in claim 15 wherein the NSAID comprises naproxen.

21. An absorbable, liquid, gel-forming composition as in claim 16 wherein the antineoplastic compound comprises paclitaxel.

22. An absorbable, liquid, gel-forming composition as in claim 17 wherein the bioactive agent comprises trapidil.

* * * * *